United States Patent
Breining et al.

(10) Patent No.: US 6,984,128 B2
(45) Date of Patent: Jan. 10, 2006

(54) METHODS FOR ENABLING AND STABILIZING TOOTH MOVEMENT

(75) Inventors: Peter M. Breining, San Mateo, CA (US); Dennis R. Stewart, Los Gatos, CA (US)

(73) Assignee: BAS Medical, Inc., San Mateo, CA (US)

( * ) Notice: Subject to any disclaimer, the term of this patent is extended or adjusted under 35 U.S.C. 154(b) by 0 days.

(21) Appl. No.: 10/695,299

(22) Filed: Oct. 27, 2003

(65) Prior Publication Data

US 2004/0115587 A1    Jun. 17, 2004

Related U.S. Application Data

(60) Provisional application No. 60/423,026, filed on Nov. 1, 2002.

(51) Int. Cl.
*A61C 7/00* (2006.01)

(52) U.S. Cl. ....................................................... 433/24
(58) Field of Classification Search .................... 433/5, 433/6, 7, 8, 20, 24, 80
See application file for complete search history.

(56) References Cited

U.S. PATENT DOCUMENTS

| | | |
|---|---|---|
| 4,153,060 A | 5/1979 | Korostoff et al. |
| 4,519,779 A | 5/1985 | Lieb |
| 4,685,883 A | 8/1987 | Jernberg |
| 4,854,865 A | 8/1989 | Beard et al. |
| 4,892,736 A | 1/1990 | Goodson |
| 4,933,183 A | 6/1990 | Sharma et al. |
| 4,959,220 A | 9/1990 | Yamamoto et al. |
| 5,085,585 A | 2/1992 | Zimble |
| 5,294,004 A | 3/1994 | Leverett |
| 5,447,725 A | 9/1995 | Damani et al. |
| 5,575,655 A | 11/1996 | Darnell |
| 5,616,315 A | 4/1997 | Masterman et al. |
| 5,633,000 A | 5/1997 | Grossman et al. |
| 5,719,197 A * | 2/1998 | Kanios et al. ........... 514/772.6 |
| 5,811,395 A | 9/1998 | Schwabe et al. |
| 5,975,893 A | 11/1999 | Chishti et al. |
| 6,048,544 A * | 4/2000 | Yue ............................ 424/443 |
| 6,322,360 B1 * | 11/2001 | Burgio ........................ 433/80 |
| RE37,656 E | 4/2002 | Bahar et al. |
| 6,607,382 B1 * | 8/2003 | Kuo et al. ...................... 433/6 |

FOREIGN PATENT DOCUMENTS

| | | | |
|---|---|---|---|
| WO | WO 95/09644 | * | 4/1995 |
| WO | WO 95/09644 A | | 4/1995 |
| WO | WO 95/09184 | * | 5/1995 |

OTHER PUBLICATIONS

Nicozisis et al., "Relaxin effects the dentofacial sutural tissues," Clinical. Orthodontics and Research., 3:192-201 (2000).

* cited by examiner

*Primary Examiner*—Todd E. Manahan
(74) *Attorney, Agent, or Firm*—Townsend & Townsend & Crew, LLP

(57) ABSTRACT

Orthodontic methods comprise applying force to reposition teeth and administering a tissue remodeling and/or an angiogenic substance(s) to the periodontal tissue surrounding the teeth to be moved. The substance(s) may be delivered before, during, or after the teeth are moved, and the substance(s) may be selectively applied only to those teeth undergoing movement at any particular time. The substance(s) may be applied from the dental repositioning appliance or may be applied separately, either topically or by injection.

15 Claims, 9 Drawing Sheets

Push Out Graph

Wiggle Test

METHODS FOR ENABLING AND STABILIZING TOOTH MOVEMENT

This application claims the benefit of prior provisional application 60/423,026, filed on Nov. 1, 2002, the full disclosure of which is incorporated herein by reference.

BACKGROUND OF THE INVENTION

1. Field of the Invention

The present invention relates generally to medical apparatus and methods. More particularly, the present invention relates to methods and systems for facilitating, accelerating, and stabilizing tooth movement before, during and after orthodontic procedures.

Orthodontic procedures suffer from four major problems. First, the braces or other appliances which effect the tooth movement must be worn for long periods of time. Second, even after a successful orthodontic treatment, the teeth often relapse towards their original positions once the braces or other treatment appliances are removed. Third, the mechanically induced movement of teeth can cause significant discomfort to the patient. Fourth, the wearing of braces is esthetically displeasing, uncomfortable, and compromises oral hygiene. While recently introduced clear plastic visible "aligners" largely overcome the latter problems, such aligners are not suitable for all patients. Moreover, the aligners do not reduce treatment time, do not reduce the risk of relapse, and do not lessen the pain associated with tooth movement in the jaw.

For these reasons, it would be desirable to provide improved orthodontic technologies for moving teeth which overcome at least some of the problems noted above. In particular, it would be desirable to provide orthodontic methods and systems which can reduce the time necessary to effect a desired tooth movement, which can reduce the pain associated with tooth movement, which can reduce the tendency of teeth to relapse to their original positions after the orthodontic treatment is stopped, and/or which can reduce the time in which unsightly braces need to be worn.

2. Description of Background Art

Nicozisis et al. (2000) *Clin. Orthod. Res.* 3:192–201, describes experiments which demonstrate the presence of endogenous relaxin in cranial tissue of mice and speculates that relaxin may be used as an adjunct to orthodontic or surgical therapy to promote manipulation of sutural tissues or affect stability. The application of electrical current to stimulate bone growth and remodeling in orthodontic procedures is described in U.S. Pat. Nos. 4,854,865; 4,519,779; and 4,153,060. Appliances for local and systematic drug delivery to the gingival tissues are described in U.S. Pat. Nos. 6,159,498, 5,633,000; 5,616,315; 5,575,655; 5,447, 725; 5,294,004; 4,959,220; 4,933,183; 4,892,736; 4,685, 883; and Re. 34,656. Polymeric shell appliances for repositioning teeth are described in U.S. Pat. No. 5,975,893. The full disclosures of each of the above U.S. patents are incorporated herein by reference.

BRIEF SUMMARY OF THE INVENTION

The present invention provides improved methods and systems for repositioning teeth in patients. In addition, the present invention provides improved methods and systems for stabilizing teeth which have already been repositioned in order to reduce or eliminate the tendency of the repositioned teeth to relapse, i.e., move back toward their prior positions. The methods for repositioning teeth comprise applying force to at least one tooth, and typically to more than one tooth and/or to different teeth over time, in the jaw of the patient. For both repositioning or stabilizing, tissue remodeling and/or an angiogenic substance(s) is administered to the patient to promote remodeling of periodontal tissue surrounding the root(s) of the tooth or teeth to be moved. Preferred substance(s) will bind to and activate the relaxin receptor in the tissues which anchor the teeth or other craniofacial structures. Most preferred is relaxin or an analog or mimetic thereof which combines tissue remodeling activity with angiogenic activity. Analogs include peptides, oligomers, fragments, etc. which comprise the active region of native relaxin and mimetics include small molecule drugs, typically below 2 kD, designed to mimic the activity of native relaxin. Alternatively, substance(s) with predominantly angiogenic activity could be selected, such as VEGF, bFGF, estrogen, nitrous oxide, naltrexone, or the like. Further alternatively, collagenases or other tissue-softening enzymes could be utilized to promote periodontal tissue remodeling according to the present invention. In some instances, it may be desirable to combine two or more tissue remodeling and/or angiogenic substance(s) having differing activities. In other instances it may be desirable to deliver different tissue remodeling and/or angiogenic substance(s) at different times during the orthodontic treatment and/or to different regions of the periodontal tissue.

The term "relaxin" means human relaxin, including intact full length relaxin or a portion of the relaxin molecule that retains biological activity [as described in U.S. Pat. No. 5,023,321, preferably recombinant human relaxin (H2)] and other active agents with relaxin-like activity, such as Relaxin and portions that retain biological activity Like Factor (as described in U.S. Pat. No. 5,911,997 at SEQ ID NOS: 3 and 4, and column 5, line 27-column 6, line 4), relaxin analogs and portions that retain biological activity (as described in U.S. Pat. No. 5,811,395 at SEQ ID NOS: 1 and 2, and column 3, lines 16–40), and agents that competitively displace bound relaxin from a receptor. Relaxin can be made by any method known to those skilled in the art, for example, as described in any of U.S. Pat. Nos. 5,759,807; 4,835,251 and co-pending U.S. Ser. No. 07/908,766 (PCT US90/ 02085) and Ser. No. 08/080,354 (PCT US94/0699).

The tissue remodeling and/or angiogenic substance(s) will be delivered at a delivery rate and a total dosage which are selected to facilitate tooth repositioning and tissue remodeling. Typically, the dosage rates will be in the range from 1 ng to 500 µg per day, usually from 10 ng/day to 20 µg/day, preferably from 20 ng/day to 10 µg/day. The dosage and other aspects of the delivery may be adjusted from time-to-time in response to the effectiveness of treatment, such as the resistance of a particular tooth or group of teeth, where the dosage might be increased if resistance is not sufficiently reduced in response to an initial dosage.

The substance(s) may be delivered at any point during the orthodontic treatment where tooth repositioning and/or tissue remodeling may be promoted. For example, the substance(s) may be applied prior to any application of force intended to move the teeth. Additionally or alternatively, the substance(s) may be applied during all or any portion of the time during which force is being applied to move the teeth. Further additionally or alternatively, the substance(s) may be applied after the teeth have been repositioned to a final desired configuration. In the latter case, application of the substance(s) may be particularly effective for promoting tissue remodeling in order to reduce the risk of relapse. In such instances, the substance(s) may be delivered using retainers or other appliances intended to help maintain the teeth in their desired final configuration. When being delivered to inhibit relapse, the remodeling and/or angiogenic substance(s) may be delivered for a limited period of time in a limited period before and/or immediately following the end of the orthodontic procedure or may be delivered continuously or periodically for long periods of time or indefinitely following the end of the orthodontic procedure. For example, the substance(s) may be delivered to some or preferably all of the regions of the gingiva where teeth have been moved in order to promote stabilization and remodeling of the tissue, usually over a period of one to eight weeks, more usually two to six weeks prior to the end of treatment.

The teeth may be repositioned by any conventional orthodontic appliance intended for applying force to move teeth. In particular, the present invention is compatible with both the use of wire and bracket systems, commonly referred to as "braces," as well as with newer systems employing removable appliances for repositioning teeth, such as the Invisalign® System, available from Align Technology, Inc., Santa Clara, Calif., and the "red, white, and blue" system available from Sybron Dental Specialties, Irvine, Calif. The present invention will also be useful with dental "positioners" which are elastomeric appliances having pre-formed tooth-receiving cavities where the patient bites into the elastomeric appliance in order to force tooth movement. Finally, the present invention may be used with dental retainers which are polymeric shell appliances typically used to maintain a final, desired tooth configuration and prevent relapse. When used with dental repositioning appliances of any type, the application of the tissue remodeling and/or angiogenic substance(s) according to the present invention will usually both facilitate tooth movement by modifying the tissue structures within the periodontal tissue which anchor the teeth and also promoting tissue remodeling which allows such tissue structures to accommodate the repositioned teeth with less tendency toward relapse.

The substance(s) of the present invention may be applied and administered in a wide variety of ways. Most simply, and as presently preferred, the substance(s) could be "painted" or otherwise topically applied to the patient's gingiva using a conventional single-use applicator such as a swab, brush, syringe, or the like. The substance(s) may be prepared in a conventional form of topical composition, such as a gel, cream, ointment, or other fluid or liquid substance. Alternatively, the substance(s) could be administered by injecting into the periodontal tissue. Additionally, the substance(s) could be delivered using a patch or other appliance which is worn on the teeth or gingiva, optionally being formed as part of the same appliance which is used to move the teeth, e.g., a bracket or removable shell appliance or retainer. In such instances, the substance(s) may be incorporated into conventional drug reservoirs which both maintain a supply of the substance(s) and which release the substance(s) at a controlled rate, over time, to target sites on the gingiva. Suitable drug delivery structures for delivering the substance(s) to the patient gingiva are described in the patent and medical literature, see, e.g., U.S. Pat. Nos. 6,159,498, 5,575,655; 5,194,003; 4,933,182; and 4,685,883, the full disclosures of which are incorporated herein by reference.

In some instances, it may be desirable to provide for enhanced penetration of the substance(s) into the gingival. For example, the substance(s) could be formulated with tissue penetration or permeation enhancers, such as dimethylsulfoxide (DMSO). Alternatively or additionally, the substance(s) can be delivered while applying energy in a manner to promote tissue penetration, including the application of an electric current in order to achieve electroporation or iontophoresis, and/or the application of ultrasound energy. The currents needed to provide for electroporation are relatively low, typically around 0.1 mA can be provided by batteries contained within the delivery structure or alternatively by external structures which are periodically applied to the gingiva or appliances present over the gingiva. Similarly, ultrasound-enhanced substance delivery can be effected by transducers incorporated into the delivery appliances and/or provided by external appliances. Suitable ultrasound conditions are from 20 kHz to 100 kHz at energy levels of one to ten $J/cm^2$.

A particular advantage of the present invention is that particular teeth can be treated with the substance(s) while other teeth in the same jaw remain untreated. In this way, those teeth which are to be moved at any point during the course of orthodontic treatment may be "relaxed" and prepared for movement while other teeth which are needed as "anchor teeth" remain untreated. In this way, the wire and bracket system, removable aligner, or the like, may be anchored on those teeth which have not been treated with the substance(s), while those teeth which are intended to be moved may be treated and more readily moved. Of course, during a normal orthodontic treatment, different teeth will be targeted for movement at different times. The present invention allows only those teeth which are intended to be moved at any particular time to be treated at that time while other teeth in the dentition remain untreated during that time and available as anchor teeth for performing the orthodontic treatment.

The present invention may also advantageously be combined with other orthodontic treatment protocols, such as electroosteogenesis where a small electrical current is applied to the gingiva or jaw to stimulate the tissues. It is believed that the combination of the substance(s) with such electroosteogenesis could provide tooth movement which is improved over that achieved with either approach alone. Moreover, the application of the electric current might act to provide "electroporation" and enhance the uptake of the substance(s) into the periodontal tissues, as described above.

In a further aspect of the present invention, improved orthodontic treatment methods are provided. The orthodontic treatment methods are of the type where at least one tooth in a patient jaw is repositioned. The improvement comprises administering at least one tissue remodeling and/or an angiogenic substance to the patient before, during, or after the force has been applied. The preferred aspects of this method are generally the same as described above.

The present invention still further provides oral delivery appliances comprising a structure and a tissue remodeling and/or an angiogenic substance(s). The structure is mountable on or over at least a portion of a patient gingiva, and the substance(s) is carried by the structure so that said substance(s) is release into at least a region of the gingiva while the structure is mounted on or over the gingiva. Typically, the delivery appliance mounts over the gingiva of an entire jaw, but in some instances it may mount over the gingiva of less than the entire jaw. Typically, the structure will include at least a portion which engages or mounts over the gingiva adjacent the roots of the target teeth, typically from one to twelve teeth, usually from one to six teeth, often from one to five teeth, and sometimes only a single tooth. The appliance may be in the form of a patch which adheres to the gingiva, a shell which is removably placeable over the teeth in the gingiva, or the like. The use of patches for delivery of the substance(s) may be particularly advantages since the patches can be cut to size in order to control dosage and/or delivery area to the gingiva. Such modified patches may be applied or adhered directly to the gingiva or alternatively may be positioned beneath a retainer which is worn to maintain the positions of the teeth. When wire and bracket orthodontic appliances are used, the delivery appliance may be formed to mount on the wire or onto the bracket, may be incorporated as part of the bracket or wire, or may be some combination thereof. The relaxin or other tissue remodeling and/or angiogenic substance may be incorporated into the oral delivery appliance in a variety of ways. Most commonly, the relaxin will be in a liquid, gel, or other releasable form which is incorporated into a time-release structure to apply the substance to the gingiva at a desired dosage rate. For example, the substance(s) may be incorporated into a porous structure and/or in a reservoir which is covered by a porous structure. In either case, the porous structure acts as a rate-controlling membrane or barrier to achieve the desired delivery rate. Alternatively, the substance(s) may be present in a biodegradable matrix which degrades in the oral environment over time to achieve a desired release rate of the substance. Suitable degradable substances include polymers, such as glycolic acid polymers and related materials.

In a still further aspect of the present invention, topical oral compositions comprise a carrier and a tissue remodeling and/or an angiogenic substance(s). The carrier is of the type which may be topically applied to a patient's gingiva, typically being in the form of a gel, cream, ointment, microemulsion or other liquid. The tissue remodeling and/or an angiogenic substance(s) may be any of the substance(s) listed above. The composition may be provided in any conventional applicator, such as a tube, syringe, bottle, or the like, and will be maintained in a sterile condition within the applicator.

DETAILED DESCRIPTION OF THE INVENTION

The present invention provides improved and facilitated orthodontic treatment by delivering tissue remodeling and/or an angiogenic substance(s) to periodontal tissue in which the teeth to be moved are rooted or anchored. As used hereinafter, "periodontal tissue" will refer to the connective tissue within the periodontal tissues, specifically including the tissue and ligaments which anchor the teeth in the bone. The application of the tissue remodeling and/or an angiogenic substance(s) to the periodontal tissue will both loosen the tissue and ligaments as well as promote remodeling of the tissue during and after orthodontic treatment.

The tissue remodeling and/or angiogenic substance(s) may be delivered to the periodontal tissue in a variety of ways, including systemic delivery, local injection, local topical application, continuously, periodically, and combinations thereof. Topical delivery is presently preferred and may be achieved using a conventional surface applicator, such as a brush, swab, syringe, squeeze tube, sponge, or other similar device. Alternatively, topical delivery may be effected using various controlled release devices, such as retainers, patches, orthodontic brackets and wires, and other appliances which may be positioned on or over the teeth and which have been modified in order to release the substance(s) to the gingiva. In some cases, it will be desired to deliver the drug into the gingival margin which is the line or groove along the gingiva-tooth interface. Substances may be applied as part of formulations which are delivered over the gingiva and/or into the sulcus. In some instances, it may be desirable to plant small substance delivery structures directly into the sulcus in a manner analogous to the delivery of antibiotics using systems, such as the PerioChip® available from Dexcel Pharma. The following specific examples of patches and structures for delivering the tissue remodeling and/or angiogenic substance(s) of the present invention are meant to be exemplary and not limiting.

Figure 1:
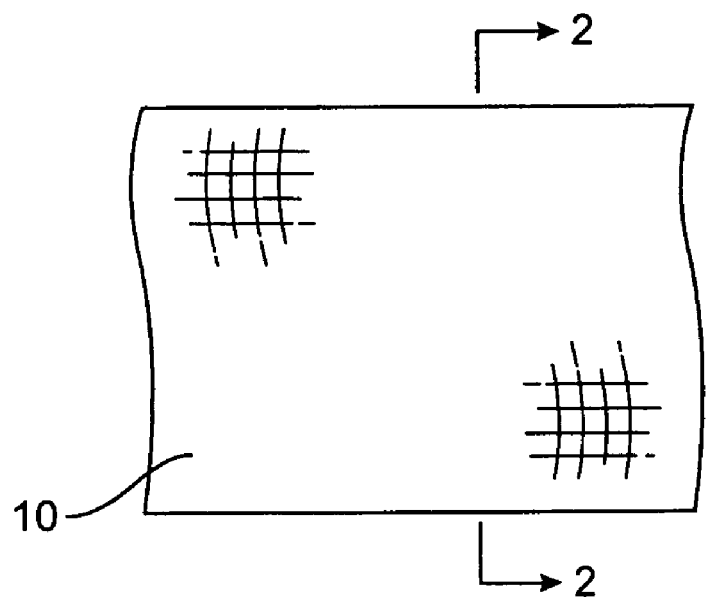
FIG. 1 illustrates an oral tissue remodeling and/or an angiogenic substance(s) delivery appliance constructed in accordance with the principles of the present invention, in the form of a patch.
Figure 2:
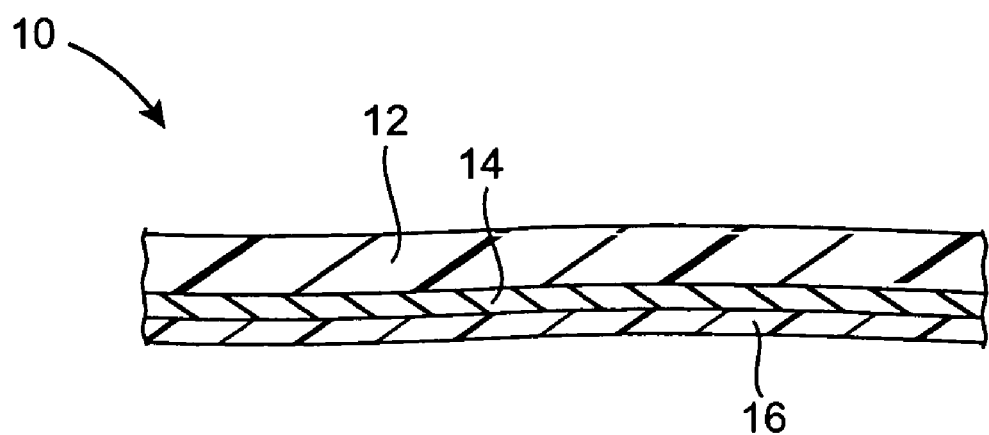
FIG. 2 is a cross-sectional view taken along line 2—2 of FIG. 1.

Referring to FIGS. 1 and 2, the substance(s) may be applied in a variety of ways, including using a patch 10 which typically comprises a reservoir layer 12, a rate controlling membrane 14, and an adhesive layer 16. A patch 10 may be cut into strips, smaller patches, or the like, and may be applied to the gingiva in order to effect topical delivery of the substance(s) from the reservoir into the tissue.

Figure 3:
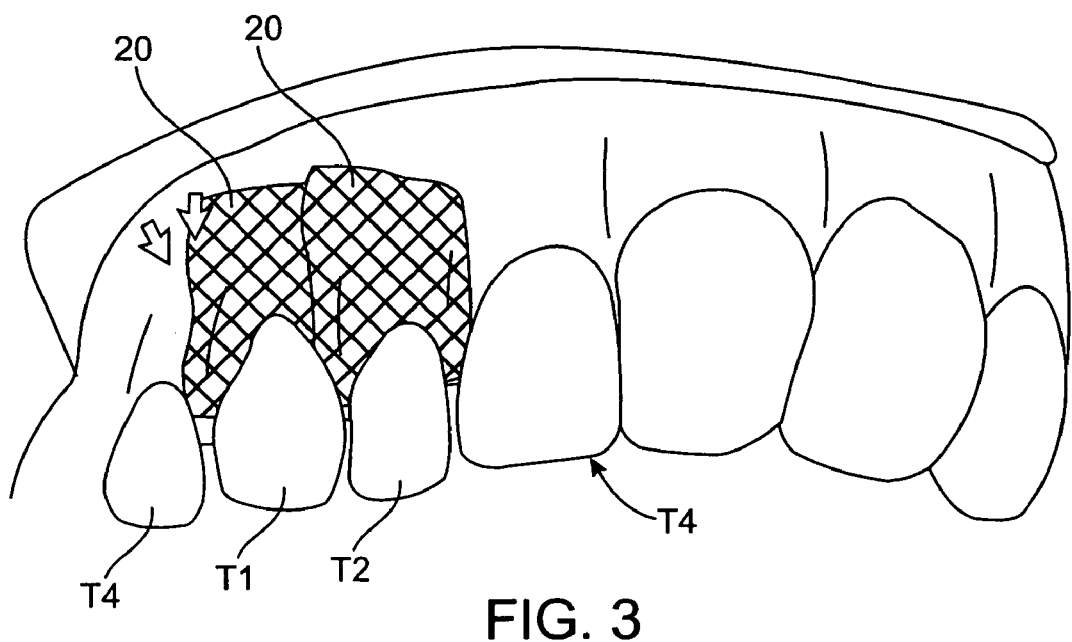
FIG. 3 illustrates the use of the patch of FIG. 1 in a first exemplary protocol according to the present invention.

As shown in FIG. 3, the patch 10 of FIG. 1 may be cut into smaller strips or pieces 20 which may be placed over the gingiva overlying individual teeth. In this way, the teeth T1 and T2, for example, may be treated to facilitate movement and promote periodontal tissue remodeling, according to the present invention, while adjacent teeth T3 and T4, as well as other non-treated teeth, remain available as anchor teeth for effecting orthodontic treatment, typically using conventional wire and bracket systems (not shown). In FIG. 3B, the positioning of the patches 20 over the roots of the teeth is shown.

Figure 4:
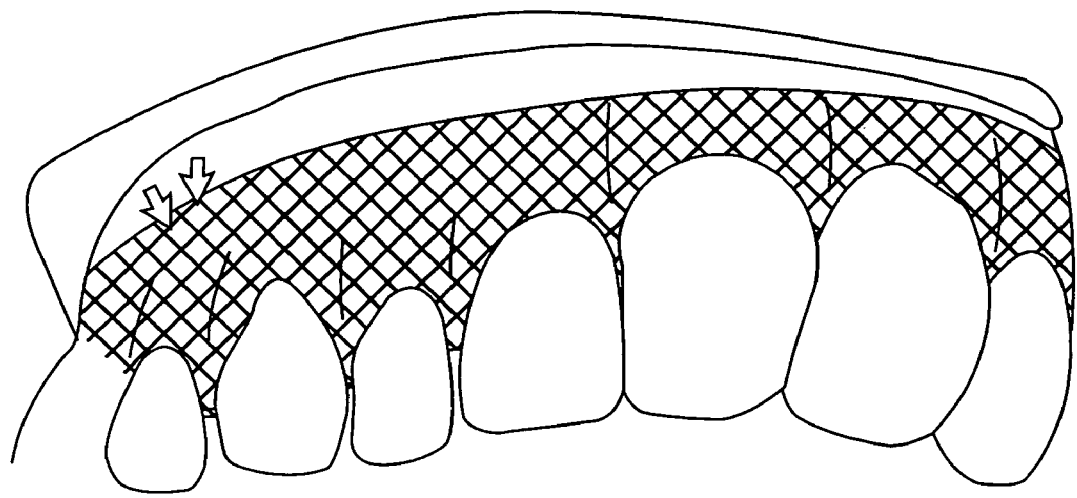
FIG. 4 illustrates the use of the patch of FIG. 1 in a second exemplary protocol according to the present invention.

In FIG. 4, a continuous strip 30 of the patch material 10 is shown placed over the gingiva of eight adjacent teeth. The strip 30, of course, could extend around the entire gingiva of one jaw. In this way, the substance(s) can be delivered to all teeth at once. Such treatment might be preferred, for example, for treating teeth after the teeth have reached their final position in order to promote tissue remodeling. Alternatively, the strip 30 could be configured so that the tissue remodeling and/or an angiogenic substance(s) are released only from particular locations on the strip to treat individual target teeth, achieving the same type of treatment as shown in FIG. 3. Although patch and strip placement in FIGS. 3 and 4 is shown only on the labial side of the gingiva, the strips could be placed additionally or alternatively on the lingual side of the gingiva.

Figure 5:
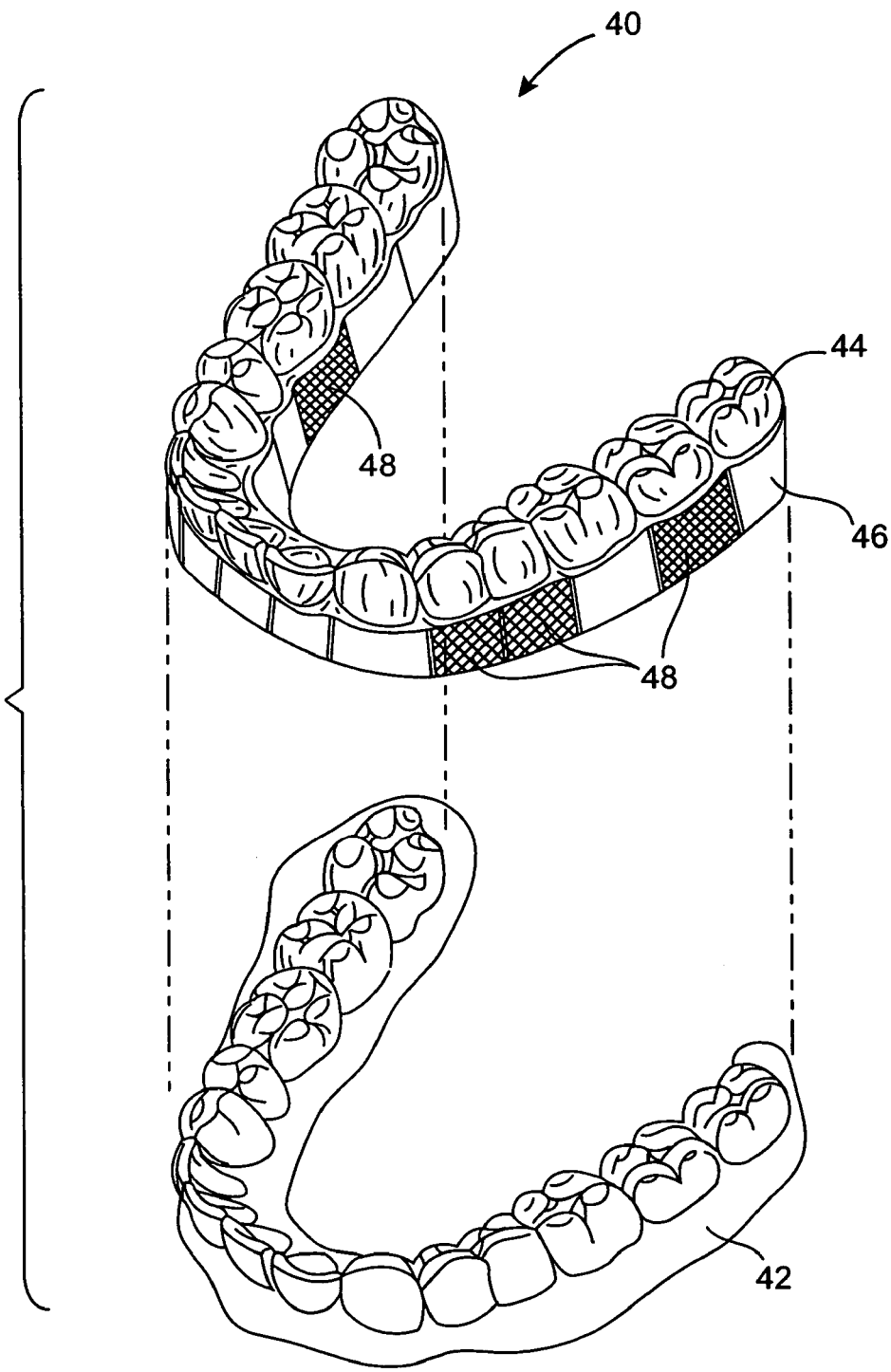
FIG. 5 illustrates the use of a polymeric shell appliance for repositioning teeth and delivering a tissue remodeling and/or an angiogenic substance(s) according to the principles of the present invention.

Referring now to FIG. 5, a dental retainer or aligner 40 is shown for placement over the dentition of a single jaw 42. A crown portion 44 of a retainer/aligner 40 is configured to be removably positionable over the teeth, while a skirt portion 46 is configured to lie over the gingiva, usually both the labial and lingual sides of the gingiva. The skirt is configured to retain and release the tissue remodeling and/or an angiogenic substance(s), either over its entire surface or over selected regions 48 as shown. In this way, the substance(s) may be selectively delivered to individual teeth or to the entire dentition in a single jaw, depending on the particular treatment protocol.

The following examples are offered by way of illustration, not by way of limitation.

EXPERIMENTAL

Two studies are presented, one examining properties of the periodontal and gingival tissues to relaxin and the second on dose finding.

I. In Vivo Studies of the Periodontal Ligament

A rat model was utilized because the rat has been historically used for many orthodontic studies. There were five animals per treatment group. Rats were treated for 1 or 3 days with human relaxin (H2 gene product) or vehicle control (Table 1 below). Relaxin or control vehicle was administered via Alzet implanted minipumps. In addition, relaxin treated rats received a 0.5 mg bolus injection (1.43 mg/kg) of relaxin at the time pumps were placed.

TABLE 1

| Days of Treatment | Control | Relaxin |
|---|---|---|
| 1 Day | C1 (n = 5) | R1 (n = 5) |
| 3 Days | C3 (n = 5) | R3 (n = 5) |

The jaws were collected for transport to the University of Washington for analysis. The day 1 jaws were delivered fresh, and the day 3 jaws were delivered frozen. Teeth from each treatment group were tested for "looseness" using a material testing device (MTD), and the periodontal ligament (PDL) was tested in a "push-out" test. The rest of the jaw was saved for histological analysis.

II. Objectives

These tests evaluated the ability of human relaxin (H2) to accelerate tooth movement during orthodontic procedures in a rat model. These studies examined the short term effects of relaxin on tooth looseness using circulating relaxin and a material testing device (MTD).

A. Tooth Looseness

Tooth displacement measured in response to a known force was measured.

B. Push-Out

Test The material properties of the PDL were measured in a material testing device to obtain force/displacement curves.

C. Histological Analysis

The contralateral jaw was used for histological analysis. Staining techniques were used to visualize collagen and elastin.

III. Protocol

A. Treatment Groups

Adult male Sprague-Dawley rats (89–94 days old) were purchased from Animal Technologies, Ltd, Livermore, Calif. There were five animals per treatment group having body weights of 300–350 grams. Rats were treated for 1 or 3 days with human relaxin (H2 gene product) or vehicle control (Table 1). Relaxin or control vehicle is administered via Alzet implanted minipumps. In addition, relaxin treated rats received a 0.5 mg bolus injection (1.43 mg/kg) at the time pumps were placed.

B. Relaxin Administration

Human relaxin (H2) produced by Connetics, Corp was administered using Alzet osmotic pumps as previously described in the rat (Garber et al. (2001) *Kidney Int.* 59: 1184–85). Relaxin was administered at a rate of approximately 8 $\mu$g/kg/hr. This delivery rate has been shown to result in a blood concentration of approximately 150 ng/ml (Garber, Microchnik et al. 2001). To ensure relaxin levels rapidly achieved effective concentrations, rats were given a bolus subcutaneous injection of 0.5 mg relaxin at the time of pump implant. Control animals received the same volume of vehicle.

C. Animal Manipulations

Animals were euthanized with anesthesia overdose at each of the specified time intervals. Maxillae were dissected into halves. One hemimaxilla was fixed in 10% formalin for 24 hours followed by decalcification in 10% EDTA for two weeks with daily changes of the solution, dehydration in increasing concentrations of ethanol, and embedding in paraffin for immunohistochemical and histomorphometric analyses. The other hemimaxilla was fixed, decalcified and frozen for the immunohistochemical analyses. Calvarias were saved for examination of sutures by similar procedures.

D. Measuring Tooth Movement

1. Push Out Test

Figure 6:
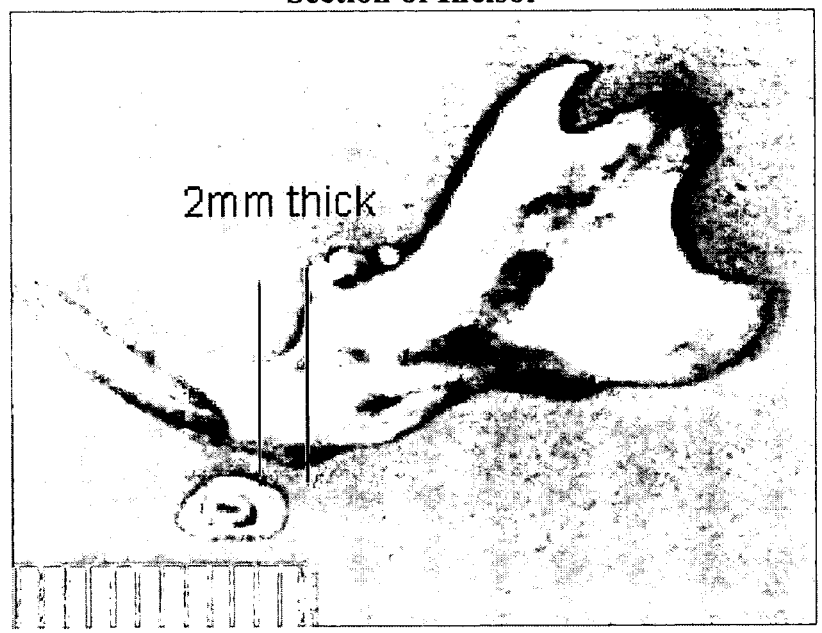
FIG. 6 is a photograph illustrating the section of the incisor which was excised for use in the push out testing described in the Experimental Section.
Figure 7:
FIG. 7 is a photograph illustrating the test equipment used for the push out testing.
Figure 8:
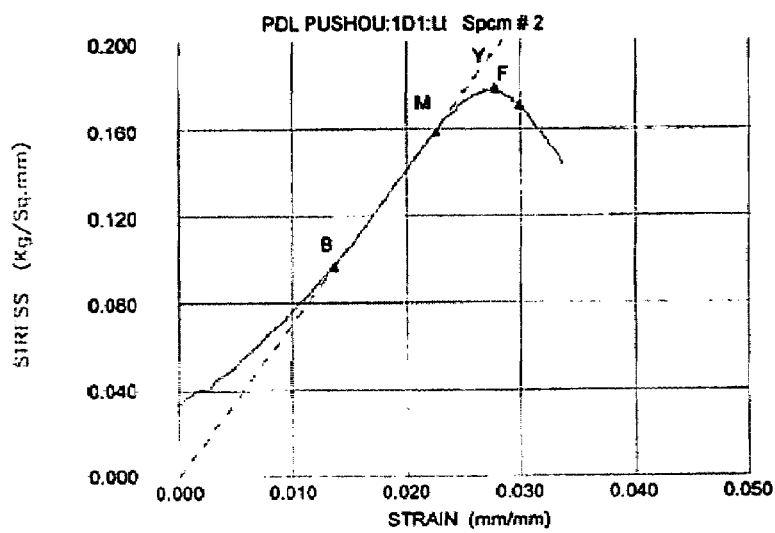
FIG. 8 is a graph showing the results of the push out testing.

Gingival tissues were dissected away, and a 2 mm disk was cut through the alveolar bone and incisor (FIG. 6). The resulting disk had alveolar bone, periodontal ligament (PDL), tooth, and pulp and was embedded in paraffin. The embedded tissue block was loaded onto a material testing device (FIG. 7) to produce the stress-strain curve shown in FIG. 8.

$$\text{Stress} = \frac{\text{load}}{\text{cross-sectional area}} = \text{kg/mm}^2$$

$$\text{Strain} = \frac{\text{elongation}}{\text{original length}} = \% \text{ elongation}$$

2. Wiggle Test

Figure 9:
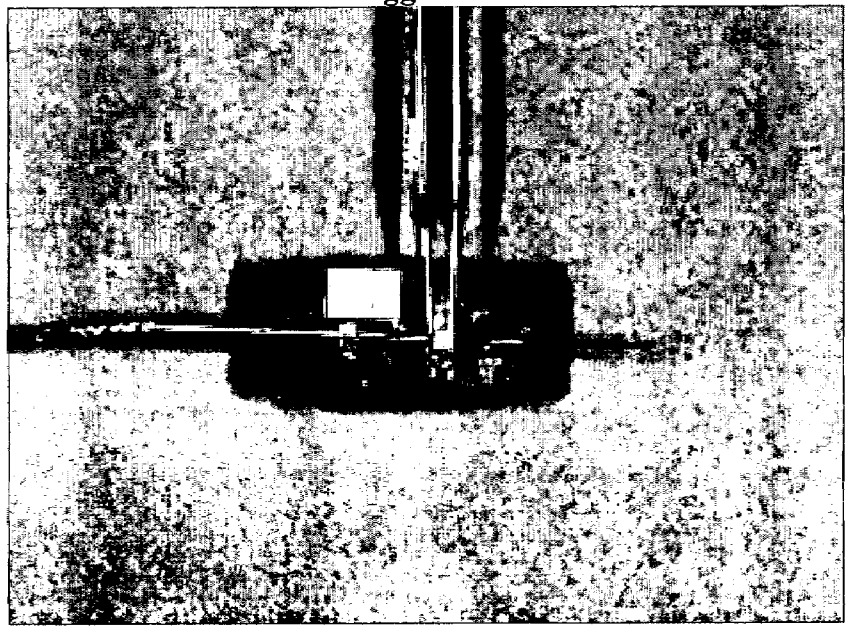
FIG. 9 is a photograph showing how the tooth wiggle testing was performed.

The second premolar tooth was embedded in paraffin and wiggled in place (FIG. 9). The amount of movement was recorded.

The resulting amount of displacement was measured repeatedly and averaged for each specimen.

IV. Results and Analysis

A. Material Testing

The material testing of the rat jaws included two different tests. These were the "push-out" test, and the "wiggle" test. Separate teeth were used for each of these tests, as explained below. The Day 1 specimens were delivered fresh while the Day 3 were frozen so are only directly comparable with the controls for that day.

1. Push-Out

Test The push-out test resulted in many different parameters of a stress strain curve. Several of the more relevant parameters were selected for the following graphs.

Figure 10:
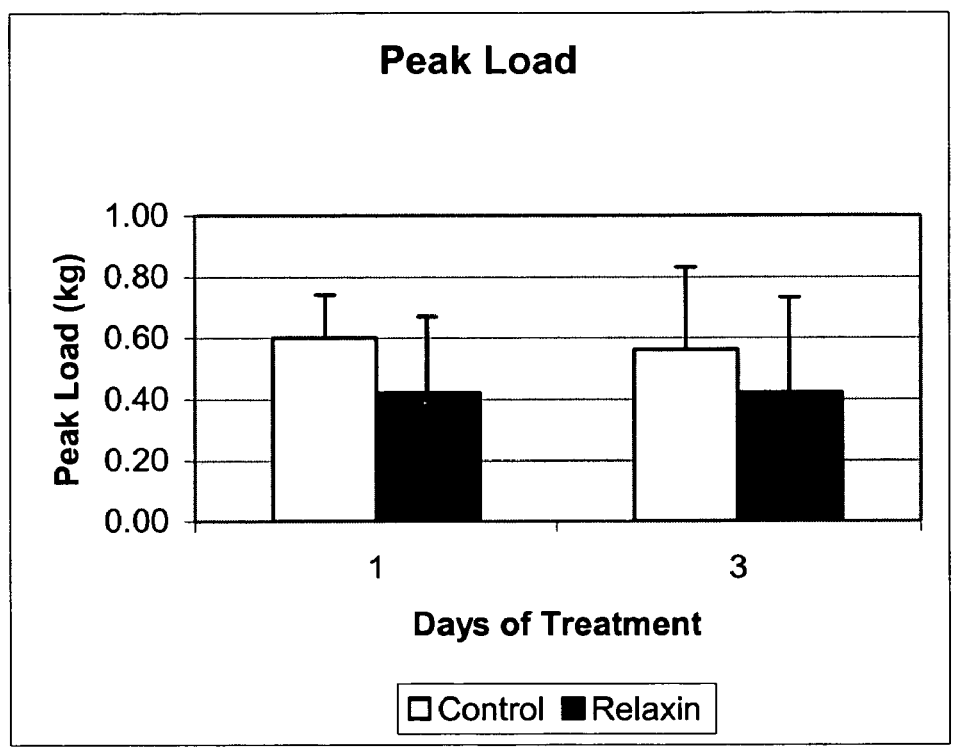
FIGS. 10–13 are graphs showing the results of the pull out testing.

Referring to FIG. 10, peak load is a measure of the maximum load (kilograms) that the PDL can withstand before breaking. The PDL appears to be "weaker" with relaxin treatment, either at day 1 or day 3 of treatment.

Figure 11:
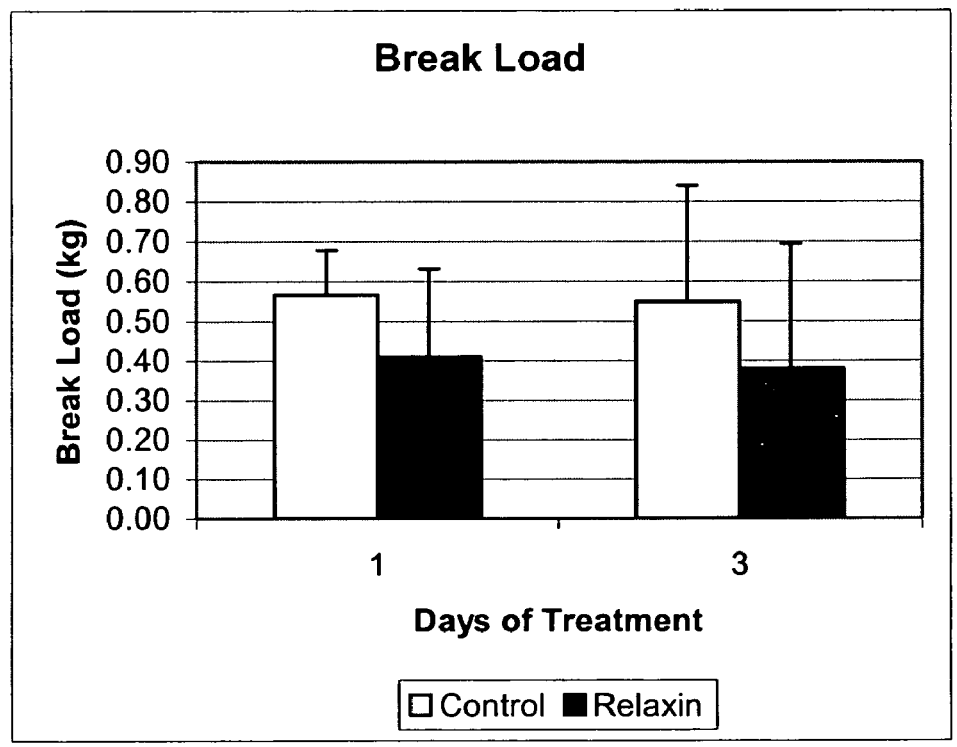

Referring to FIG. 11, break load is the force in kilograms needed to break the PDL. It was observed that the force was less with relaxin treatment, indicating a softening of the ligament.

Figure 12:
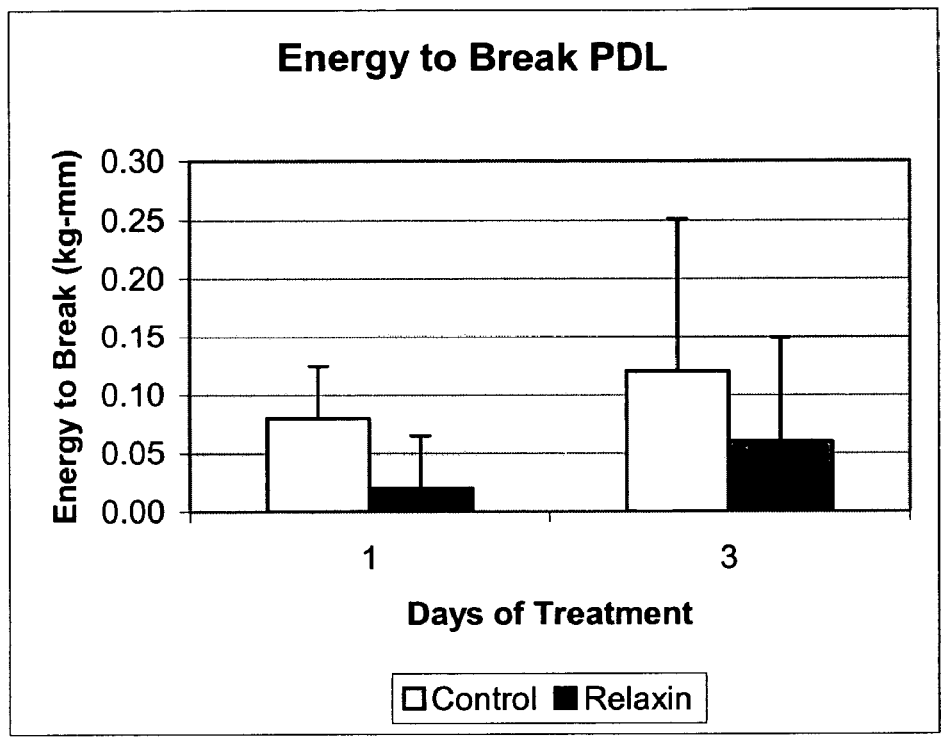

Referring to FIG. 12, energy is the area under the curve of the force needed to break the PDL. Again, relaxin resulted in less energy needed to break the PDL indicating its lessened resistance to force.

Figure 13:
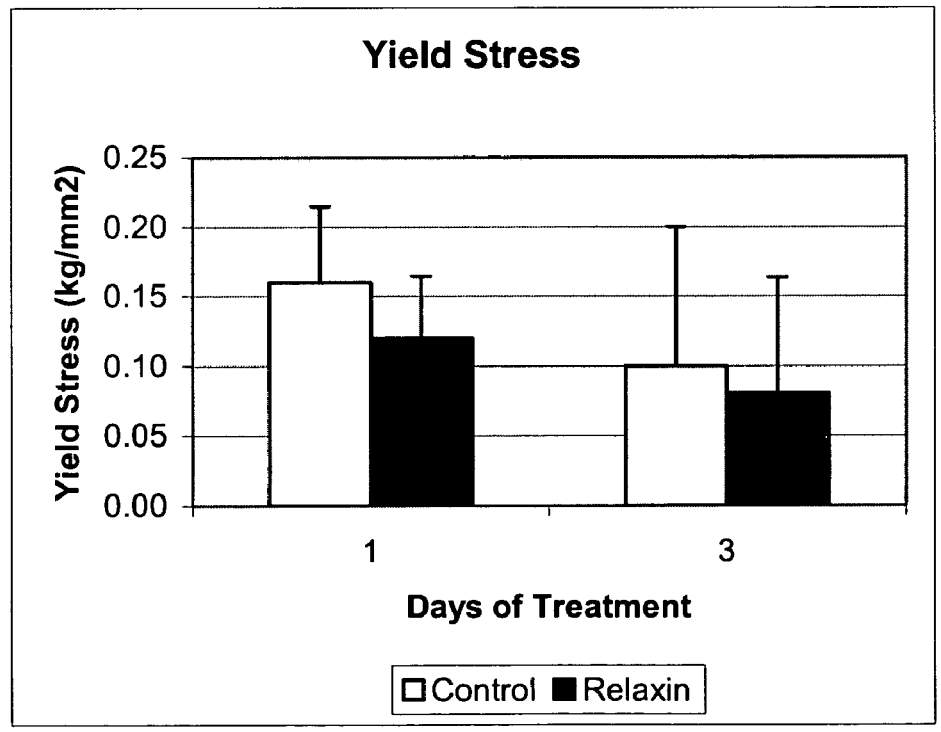

Referring to FIG. 13, yield stress is the amount of stress (kilograms/square mm) needed to cause the PDL to yield. The effect of relaxin was to lower this parameter, indicating the ligament was softer.

2. Tooth Wiggle

Figure 14:
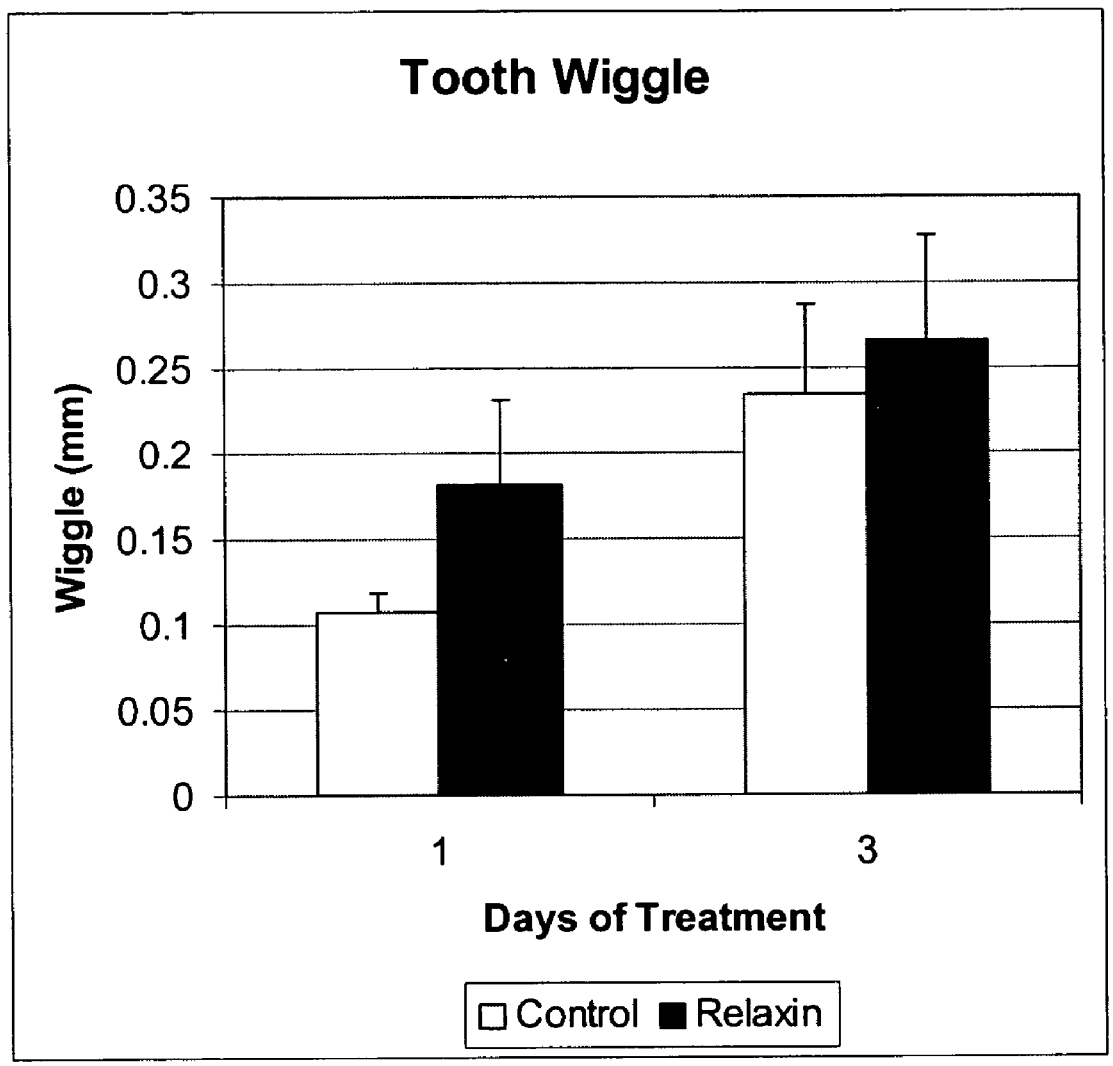
FIG. 14 is a graph showing the results of the tooth wiggle testing.

Referring to FIG. 14, the tooth wiggle test demonstrated that the tooth was looser in the relaxin treated animals. This was especially prominent in the day 1 treated animals. The smaller difference seen on day 3 may be due to freezing the tissue.

B. Histological Analysis

The specimens were decalcified, embedded, sectioned and strained with a variety of histological stains. The PDL and gingival connective tissue were examined for a reduction and/or reorganization in the collagen. Collagen normally has a highly regular structure, which can be observed under a microscope using polarized light. Intact collagen demonstrates a birefringence or glow which is lost upon breakdown of the collagen.

Comparison of the treated collagen with the untreated control, under polarized label, demonstrated that the relaxin had broken down the collagen. In the relaxin treated animals, the collagen fibers have been shortened and no longer have the parallel arrangement.

V. Dose Finding Experiment

Figure 15:
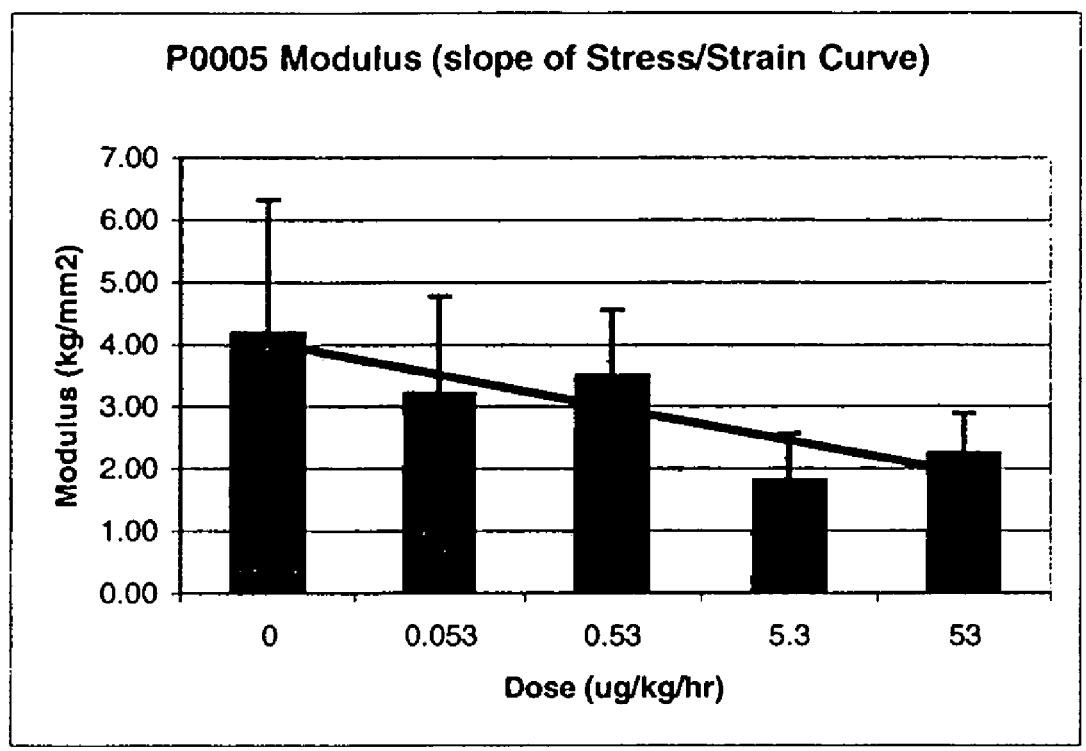
FIG. 15 illustrates the results of the dose response testing.

The following test helps determine an effective dose of relaxin for modification of collagen in the PDL and gingival tissues. Relaxin was administered in different doses to the rat for 5 days via Alzet subcutaneous pumps. Again the material testing device was used for measurement of the effects of relaxin. The results are shown in FIG. 15.

The modulus is the slope of the stress strain graph. This figure suggests a dose relationship of relaxin with the softening of the PDL. It appears that even the lowest dose had modest effects on the PDL, indicating that a small amount of relaxin would be effective.

VI. Summary of Data

These data demonstrate for the first time that relaxin is effective in vivo in modifying the mechanical characteristics the ligaments that hold the tooth in the jaw. Major effects appear to be on the collagen which comprises a large portion of the PDL and gingival fibers. Relaxin affects these fibers as demonstrated by histological and physical measurements. The result of this modification of PDL and gingival fibers is to accelerate tooth movement and prevent relapse. Our data on dose indicate that even small amounts of relaxin may be effective in achieving these effects.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for preventing relapse in a patient, said method comprising:
   applying force to at least one tooth in a jaw of the patient, and
   administering a tissue remodeling and/or an angiogenic substance to the patient to promote remodeling of gingiva surrounding the tooth, wherein said tissue remodeling and/or angiogenic substance is administered to the patient at a dose from about 1 ng to about 500 µg per day.

2. The method of claim 1, wherein said remodeling and/or angiogenic substance is relaxin or an analog or mimetic thereof.

3. The method of claim 2, wherein said relaxin is delivered to the patient for a period of time before, after or during an orthodontic procedure to some or all of the regions of the gingiva where teeth have been moved in order to promote stabilization and remodeling of the gingiva.

4. The method of claim 2, wherein said relaxin is delivered to the gingiva by a topical composition selected from the group consisting of gel, cream, ointment, and fluid substance.

5. The method of claim 2, wherein said relaxin is injected into the gingiva.

6. The method of claim 2, wherein said relaxin is released from a controlled release device engaged against the gingiva.

7. The method of claim 1, wherein said applying force comprises positioning a removable appliance between one or more anchor teeth and one or more target teeth.

8. The method of claim 7, wherein applying force further comprises adjusting said appliance, wherein said appliance is selected from the group consisting of positioners, aligners, and retainers.

9. The method of claim 7, wherein the removable appliance comprises a reservoir which releases the substance.

10. The method of claim 9, wherein the reservoir further comprises a porous structure which releases the substance at a controlled rate over time onto the gingiva of the patient.

11. The method of claim 1, wherein said remodeling and/or angiogenic substance is applied to the gingiva while force is applied to at least one tooth in the jaw of the patient.

12. The method of claim 1, wherein said remodeling and/or angiogenic substance is applied to the gingiva after force is applied to at least one tooth in the jaw of the patient.

13. The method of claim 1, wherein said remodeling and/or angiogenic substance is applied to the gingiva before force is applied to at least one tooth in the jaw of the patient.

14. The method of claim 1, wherein the angiogenic substance is selected from the group consisting of VEGF, bFGF, estrogen, nitrous oxide and naltrexone.

15. The method of claim 1, wherein the patient undergoes orthodontic treatment.

* * * * *